United States Patent [19]

Gressel et al.

[11] Patent Number: 4,826,871

[45] Date of Patent: May 2, 1989

[54] TOPICAL OPHTHALMIC COMPOSITIONS CONTAINING ONE OR MORE RETINOIDS

[76] Inventors: Philip D. Gressel, 551 Chambers Creek Dr., Everman, Tex. 76140; Robert E. Roehrs, 3729 Hulen Park, Fort Worth, Tex. 76109; John L. Ubels, 2862 N. 55th St., Milwaukee, Wis. 53210; Henry F. Edelhauser, 12765 W. Brentwood Dr., New Berlin, Wis. 53151

[21] Appl. No.: 935,477

[22] Filed: Nov. 26, 1986

Related U.S. Application Data

[63] Continuation-in-part of Ser. No. 711,424, Mar. 13, 1985, abandoned.

[51] Int. Cl.$^4$ .................. A61K 31/38; A61K 31/34; A61K 31/07; A61K 31/11
[52] U.S. Cl. .................................... 514/438; 514/461; 514/544; 514/559; 514/678; 514/701; 514/717; 514/725; 514/915
[58] Field of Search ............... 514/570, 559, 438, 461, 514/544, 701, 717, 725, 678, 915

[56] References Cited

U.S. PATENT DOCUMENTS

| | | | |
|---|---|---|---|
| 3,506,760 | 4/1970 | Brod | 424/253 |
| 3,843,782 | 10/1974 | Krezanoski et al. | 424/78 |
| 3,920,810 | 11/1975 | Rankin | 424/80 |
| 3,987,163 | 10/1976 | Rankin | 424/78 |
| 4,039,662 | 8/1977 | Hecht et al. | 424/180 |
| 4,131,651 | 12/1978 | Shah et al. | 424/78 |
| 4,219,545 | 8/1980 | Collins | 424/181 |

FOREIGN PATENT DOCUMENTS

| | | |
|---|---|---|
| 844544 | 1/1977 | Belgium . |
| 0077197 | 4/1983 | European Pat. Off. . |
| 1431841 | 9/1973 | United Kingdom . |
| 1430223 | 3/1976 | United Kingdom . |

OTHER PUBLICATIONS

Chem. Abst. 87:102,063m (1977)–Chang et al.
Chem. Abst. 90:203,707s (1979)–Chan et al.
Chem. Abst. 91:117,154y (1979)–Pawson et al.
Chem. Abst. 92:146,995z (1980)–Chan et al.
Chem. Abst. 96: 406u (1982)–Lovey et al.
ArVa–1984–Ubel et al., -3–9:00, "Vitamin A is Present as Retinol in Tears".
Dispersa–Therapeutic Index–Feb. 1981.
Tseng, "Topical Vitamin A Treatment for Dry Eye Disorders", Science Writers Seminar in Ophthalmology, 9-30-10-3, Research to Prevent Blindness, pp. 1–6 (1984).
Sommer et al., "Topical Retinoic Acid in the Treatment of Corneal Xerophthalmia", *Am. Journal of Ophthalmology*, vol. 86, pp. 615–617 (1978).
Van Horn et al., "Topical Retinoic Acid in the Treatment of Experimental Xerophthalmia in the Rabbit", *Archives of Ophthalmology*, vol. 99, pp. 317–321, 1981.
Pirie, "Effects of Locally Applied Retinoic Acid on Corneal Xerophthalmia in the Rat", *Experimental Eye Research*, vol. 25, pp. 297–302 (1977).
Ubels et al., "Healing of Experimental Corneal Wounds Treated with Topically Applied Retinoids", *Am. Journal of Ophthalmology*, vol. 95, pp. 353–358 (1983).
Smolin et al., "Tretinoin and Corneal Epithelial Wound Healing", *Archives of Ophthalmology*, vol. 97, pp. 545–546 (1979).
Hatchell et al., "Treatment of Xerophthalmia with Retinol, Tretinoin and Etretinate", *Archives of Ophthalmology*, vol. 102, pp. 926–927 (1984).
Grosz, "Local Use of Vitamin A Preparations in Ophthalmic Practice", *Archives of Ophthalmology*, vol. 5, pp. 727–734 (1939).
Sommer, "Treatment of Corneal Xerophthalmia with Topical Retinoic Acid", *Am. Journal of Ophthalmology*, vol. 95, pp. 349–352 (1983).
Hatchell et al., "Corneal Epithelial Wound Healing in Normal and Diabetic Rabbits Treated with Tretinoin", *Archives of Ophthalmology*, vol. 103, pp. 98–100 (1985).
Tseng et al., "Topical Retinoid Treatment for Various Dry–Eye Disorders", *Ophthalmology*, vol. 92, pp. 718–727 (1985).

*Primary Examiner*—Douglas W. Robinson
*Attorney, Agent, or Firm*—James A. Arno; Gregg C. Brown

[57] ABSTRACT

Topical ophthalmic compositions containing one or more retinoids selected from the group consisting of near and remote analogues and derivatives of retinoic acid are described. Six classes of ophthalmic vehicles suitable as carriers for the retinoids are also described. The compositions are useful in the treatment of dry eye syndrome and related ophthalmic surface disorders and as ocular lubricants. A method of treating dry eye syndrome and related ophthalmic surface disorders and a method of providing topical ocular lubrication using these compositions are also described.

6 Claims, No Drawings

TOPICAL OPHTHALMIC COMPOSITIONS CONTAINING ONE OR MORE RETINOIDS

CROSS REFERENCE TO RELATED APPLICATION

This application is a continuation-in-part of U.S. patent application Ser. No. 711,424, filed Mar. 13, 1985, now abandoned.

BACKGROUND OF THE INVENTION

1. Field of the Invention

The present invention relates to topical ophthalmic compositions which act as ocular lubricants and are useful in the treatment of dry eye syndrome and related ophthalmic surface disorders. More particularly, this invention relates to ophthalmic compositions having the above-identified utility which comprise one or more retinoids selected from the group consisting of near and remote analogues and derivatives of retinoic acid, and a pharmaceutically acceptable ophthalmic vehicle.

2. Discussion of Related Art

The problems associated with dry eye syndrome and related eye ailments associated with inadequate lubrication of the eye have been the subject of considerable discussion in the scientific and patent literature. For example, these problems are discussed in U.S. Pat. Nos. 4,131,651; 4,039,662; 3,987,163; 3,920,810; and 3,843,782; and Belgian Patent No. 844,544. The contents of these patents relating to dry eye syndrome and related surface disorders are incorporated herein by reference.

The above-cited patents disclose formulations which are said to relieve the symptoms associated with dry eye syndrome. However, none of these prior art formulations meet all of the important criteria for an effective and long lasting treatment of dry eye syndrome, particularly the moderate to serve keratoconjunctivitis sicca (KCS) patient. These prior art attempts fall into three categories corresponding to their physical state: liquids, anhydrous ointments, and solids. The solids are in the form of ocular inserts which slowly dissolve or erode to provide a thickened tear film. While these have the potential for providing longer term symptomatic relief than liquids, few patients are willing to persist in using them since they are difficult to insert and, once in place, tend to be uncomfortable, frequently themselves causing the foreign body sensation they were meant to treat. Prior liquid and ointment formulations, while giving the sensation of relief, are strictly palliatives without long-term effect.

A further description of the physical manifestations associated with dry eye disorders is seen in a scientific paper presented by Scheffer Chuei-Goong Tseng at the Science Writers Seminar in Ophthalmology, sponsored by Research to Prevent Blindness, Inc., held in Washington, D.C., Sept. 30 to Oct. 3, 1984: Tseng, "Topical Vitamin A Treatment for Dry Eye Disorders", pages 1-6 (1984). The Tseng article describes experiments in which an ointment containing Vitamin A is utilized to treat dry eye disorders associated with Sjogrens's Syndrome and Stevens-Johnson Syndrome.

Still further description concerning dry eye disorders is presented in commonly assigned U.S. patent application Ser. Nos. 700,861 and 695,364 filed Jan. 23, 1985, which are based on International Applications Nos. PCT/US83/00841 and PCT/US83/00840 filed May 25, 1983, respectively; the entire contents of these applications are incorporated herein by reference. These applications are directed to the use of ophthalmic solutions and gels based on polyanionic polymers for the treatment of dry eye disorders. The compositions of the present invention differ from the solutions and gels described in these related applications in that, inter alia, the compositions of the present invention contain one or more retinoids.

Certain retinoids have been previously identified as being useful in the treatment of various ophthalmic disorders. For example, U.S. Pat. No. 3,506,760 discloses oral compositions containing caffeine and beta-carotene (10,000 to 100,000 International Units of Vitamin A activity), and indicates that oral administration of theses compositions provides an effective treatment for night blindness. British patent specification No. 1,430,223 discloses topical anti-inflammatory preparations which contain a steroid as a principal active ingredient, along with other ingredients such as antimicrobial and keratolytic agents; retinoic acid is disclosed as a possible keratolytic agent. This patent does not provide any teaching concerning the use of retinoids in ocular lubricant preparations for treating dry eye syndrome and related ophthalmic disorder. British patent specification No. 1,431,841 discloses the use of ophthalmic-nutritional preparations for the treatment of ophthalmic disorders caused by a Vitamin A deficiency. These preparations contain Vitamin A and other vitamins, and are indicated as being useful when taken orally or applied topically. This reference does not provide any teaching concerning ocular lubricants suitable for the topical treatment of dry eye syndrome. European patent application No. EP 0 077 197 A1 discloses the use of retinoic acid in combination with methotrexate to prevent proliferation of remnant lens epithelial cells.

The use of topically applied retinoic acid in the treatment of xerophthalmia, an ophthalmic disorder caused by Vitamin A deficiency and characterized by a dryness of the conjunctiva and cornea, is discussed in the following articles: Sommer, et al, "Topical Retinoic Acid in the Treatment of Corneal Xerophthalmia", *American Journal of Ophthalmology*, Vol. 86, pages 615–617 (1978); Van Horn, et al, "Topical Retinoic Acid in the Treatment of Experimental Xerophthalmia in the Rabbit", *Archives of Ophthalmology*, Vol. 99, pages 317–321 (1981); and Pirie, "Effects of Locally Applied Retinoic Acid on Corneal Xerophthalmia in the Rat", *Experimental Eye Research*, Vol. 25, pages 297–302 (1977). These articles discuss the use of topical retinoic acid therapy in conjunction with systemic administration of Vitamin A to treat xerophthalmia. This discussion does not indicate that topically applied retinoids alone would be effective in the treatment of dry eye disorders and as ocular lubricants.

The use of topically applied retinoids to promote healing of corneal wounds is discussed in the following article: Ubels, et al, "Healing of Experimental Corneal Wounds Treated with Topically Applied Retinoids", *American Journal of Ophthalmology*, Vol. 95, pages 353–358 (1983). This discussion indicates that the retinoids were dissolved in ethanol and then combined with corn oil. The final formulations are described as solutions which contain "not more than 2% ethanol in corn oil".

Two recent developments in connection with the use of retinoids in topical ophthalmic preparations are described in copending and commonly assigned U.S. patent application Ser. Nos. 711,345 and 711,419, both of which were filed on Mar. 13, 1985; the entire contents of these copending application are incorporated herein by reference. These developments may be more particularly described as relating to novel topical ophthalmic compositions containing one or more retinoids selected from the group consisting of retinol, dehydroretinol, retinal, and retinoic acid and its isomers, and to the use of these compositions in the treatment of dry eye syndrome and related ophthalmic surface disorders and as ocular lubricants. The inventions described and claimed in these copending applications differ from the present invention in that, inter alia, the compositions of the present invention contain different retinoids which are not believed to have been previously utilized in ophthalmic preparations.

Three prior art problems associated with ophthalmic compositions containing one or more retinoids have been the poor solubility of retinoids, the instability of pharmaceutical compositions containing these compounds, and the irritation frequently associated with topical application of these compositions to the eye. The present invention is directed to solving these and other problems.

SUMMARY OF THE INVENTION

A principal object of the present invention is the provision of topical ophthalmic compositions which are useful in treating the symptoms associated with dry eye syndrome and related ophthalmic surface disorders, and which have a topical ocular lubricating effect.

Another object of the present invention is the provision of a method for treating dry eye syndrome and related ophthalmic surface disorders and a method of providing topical lubrication to the eye.

The foregoing objects and other general objects of the present invention are satisfied by the provision of topical ophthalmic compositions comprising an effective amount of one or more retinoids selected from the group consisting of near and remote analogues and functional derivatives of retinoic acid which may be biotransformed into an active form, and a pharmaceutically acceptable ophthalmic vehicle. The present invention also provides a method of treating dry eye syndrome and related ophthalmic surface disorders and a method of providing topical lubrication to the eye utilizing such compositions.

DETAILED DESCRIPTION OF THE INVENTION

The topical ophthalmic compositions of the present invention contain an effective amount of one or more retinoids as a principal active ingredient. The specific retinoid compounds which may be utilized in the ophthalmic compositions of the present invention include near and remote analogues and functional derivatives of retinoic acid which may be biotransformed into the active form of the retinoid. Such compounds are described in the following U.S. Pat. Nos.: 4,395,575; 4,335,248; 4,299,995; 4,231,944; 4,216,312; and 4,171,318. The contents of these patents relating to the structure, synthesis and physical properties of these compounds are incorporated herein by reference. Any references to the term "retinoid" or variations thereof throughout the remainder of this specification are intended to include all such compounds, as well as all pharmaceutically acceptable salts of these compounds.

The preferred retinoids include those of formula:

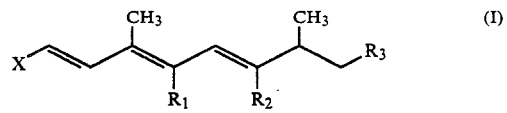

wherein:

$R_1$ and $R_2$ are selected from hydrogen and fluorine, provided that if one of $R_1$ and $R_2$ is fluorine the other is hydrogen;

$R_3$ is selected from formyl, hydroxymethyl, alkoxymethyl, carboxyl, alkoxycarbonyl, carbamoyl, mono(-lower alkyl)-carbamoyl and di(lower alkyl)-carbamoyl; and X is selected from

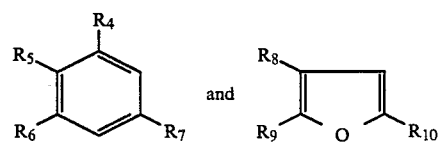

wherein:

at least one of $R_4$, $R_5$ and $R_7$ is halogen and the other are hydrogen or lower alkyl;

$R_6$ is selected from lower alkyl and lower alkoxy;

$R_8$ and $R_{10}$ are each lower alkyl; and $R_9$ is selected from hydrogen and lower alkyl, or pharmaceutically acceptable salts thereof; and those of formula:

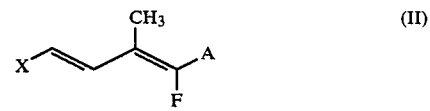

wherein:

A is selected from —CH$_2$OH and —CHO; and
X is selected from

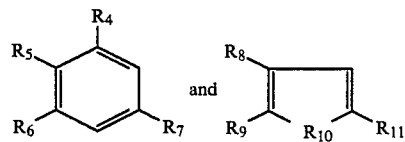

wherein:

at least one of $R_4$, $R_5$ and $R_7$ is halogen and the others are hydrogen or lower alkyl;

$R_6$ is lower alkyl or lower alkoxy;

$R_8$ and $R_{11}$ each are lower alkyl;

$R_9$ is hydrogen or lower alkyl; and $R_{10}$ is oxygen or sulphur, or pharmaceutically acceptable salts thereof.

The retinoids are preferably contained in the preparations of the present invention in an amount of from about 0.00001% to about 0.01% by weight, more preferably in an amount of from about 0.00001% to about 0.001% by weight. It has been discovered that even very low concentrations of retinoids in these ranges are effective in treating dry eye syndrome and providing ocular lubrication. The surprising effectiveness of such low concentrations is significant, because at these concentrations the incidence of patient complaints of ocular irritation attributable to the topical application of retinoids to the eye is expected to be much less.

The compositions of the present invention comprise one or more retinoids in combination with a pharmaceutically acceptable ophthalmic vehicle. Suitable ophthalmic vehicles include the following classes of vehicles: substantially nonaqueous liquid vehicles; substantially nonaqueous semisolid vehicles; solid vehicles and devices; aerosol vehicles; liquid and semisolid vehicles containing oil or lipid material and a substantial amount of water in the form of a dispersion or mixture; and substantially aqueous vehicles. These vehicles are described in greater detail below.

The first class of vehicles is made up of substantially nonaqueous liquid vehicles. These vehicles may contain one or more of the above-described retinoids either dissolved or suspended therein, preferably dissolved therein. The specific vehicles of this class include: vegetable and mineral oils, such as, liquid petrolatum, corn oil, castor oil, sesame oil, peanut oil, and so on; triglycerides, such as the capric/caprylic triglycerides commonly used in foods and cosmetics; liquid lanolin and lanolin derivatives; perfluorohydrocarbons; and combinations of the foregoing vehicles.

The second class of vehicles is made up of substantially nonaqueous semisolid vehicles, such as ointments. The retinoids may be suspended or dissolved in such vehicles. Specific examples of suitable vehicles in this class include: various types of petrolatum, such as white, yellow, red and so on; lanolin and lanolin derivatives; gelled mineral oil having a hydrocarbon base, such as PLASTIBASE TM; petrolatum and ethylene carbonate mixtures; petrolatum in combination with surfactants and polyglycol, such as polyoxyl 40 stearate and polyethylene glycol; and combinations of the foregoing vehicles. These vehicles may be combined with oils and/or waxes to vary consistency and enhance retinoid solubility.

The third class of vehicles is made up of solid vehicles or devices. Examples of such vehicles include non-erodible devices which are inserted into the conjunctival sac of the eye and later removed, such as the Alza-type diffusion or osmotic pressure controlled polymer membranes; and bioerodible polymers which do not have to be removed from the conjunctival sac, such as essentially anhydrous but water soluble polymers and resins (e.g., celluloses, polycarboxylic acids, and so on).

The fourth class of vehicles is made up of aerosols, wherein the retinoids are suspended or dissolved in a suitable gas or liquid propellant, such as Propellants 11 and 12, and are delivered via a metered-type valve.

The fifth class of vehicles is made up of liquid and semisolid vehicles which comprise oil or lipid material and a substantial amount of water in the form of a dispersion or mixture. Examples of such vehicles include: phospholipid dispersions, liquid or semisolid water-in-oil emulsions, liquid or semisolid oil-in-water emulsions, and mixtures of the above. Ophthalmic vehicles containing a phospholipid emulsifying agent are described in copending and commonly assigned U.S. patent application Ser. No. 711,550, filed Mar. 13, 1985; the entire contents of this copending application are incorporated herein by reference. The vehicles described in this copending application represent the preferred vehicles of this class.

The sixth class of vehicles is made up of substantially aqueous vehicles. The vehicles of this class include: aqueous solutions which optionally contain cosolvents such as glycols and surfactants; aqueous solutions of the type just described which further comprise viscosity building agents, such as methylcellulose, polyvinyl alcohol (PVA), Carbopol, and so on; and medium to high viscosity polymer-based gels which increase the ocular residence time of the vehicle, such as gels based on Carbopol, cellulosics, and combinations thereof. The preferred vehicles of this class are based on polyanionic polymers; such vehicles are described in greater detail in the above-cited U.S. patent application Ser. Nos. 700,861 and 695,364, the contents of which have been incorporated herein by reference.

The only limitations with respect to the use of particular ophthalmic vehicles are that these vehicles be compatible with the retinoids contained therein and facilitate the above-described utility of the present formulations in treating dry eye syndrome and related ophthalmic surface disorders and providing topical ocular lubrication.

The stability of the retinoids contained in the compositions of the present invention is generally enhanced when antioxidants and/or opaquing agents are added to the preparations. It is therefore preferred that such stabilizing agents be added to the preparations. The compositions of the present invention preferably contain an antioxidant to protect the retinoid component of the compositions from oxidative degradation. Examples of suitable antioxidants include: propyl gallate, hydroquinone, butylated hydroxytoluene (BHT), butylated hydroxyanisole (BHA), ascorbyl palmitate, acetyl cysteine, ascorbic acid, nordihydorguaiaretic acid (NDGA), sodium bisulfite, and combinations thereof. The preferred antioxidants are propyl gallate, BHA, BHT and hydroquinone, with propyl gallate being particularly preferred. Such antioxidants are typically employed in an amount of 0.0005% to 1.0% by weight. The compositions of the present invention may also require an opaquing agent to protect the retinoid component from photolytic deactivation. Examples of suitable opaquing agents include: titanium dioxide and silicon dioxide. Such opaquing agents are typically employed in an amount of 0.01% to 1.0% by weight.

The compositions of the present invention may also include conventional ingredients such as neutralizing agents and tonicity agents, as described in more detail below.

The compositions of the present invention which utilize polyanionic polymers as the vehicle preferably also contain a polymer stabilizing agent. The preferred stabilizing agents are polyols. These agents are utilized in an amount of from about 0.2% to 5% by weight. Representative examples of such polyols include: mannitol, sorbitol, glycerol, sucrose, related sugars, and the like. An especially preferred stabilizing agent is mannitol at a concentration of from 0.2% to 5% by weight.

Ophthalmic products are packaged in multiple use containers as a general rule. Preservatives may be included in the preparations of the present invention to prevent contamination of the preparations when they are exposed to microorganisms during use. Examples of suitable preservatives include: benzalkonium chloride, thimerosal, chlorobutanol, chlorhexidine, methylparaben, propylparaben, phenylethyl alcohol, sorbic acid, Onamer M (Onamer M is available from Onyx Chemical Company, Jersey City, N.J.), other agents known to those skilled in the art, and combinations thereof. Such preservatives are typically employed in an amount of from about 0.0005% to 1.0% by weight. If no preservative is desired, the preparations may be sterile packaged in unit-of-use containers. With respect to the use of Onamer M, the contents of commonly assigned U.S. Pat. No. 4,407,791 are incorporated herein by reference.

The compositions of the present invention which utilize substantially aqueous vehicles may be neutralized to the desired pH with basic chemicals such as sodium hydroxide, ammonium hydroxide, ethanolamine, urea, and selected amines. Mineral acids such as hydrochloric, phosphoric or sulfuric may be used to adjust pH toward acidity. The preferred pH range is from 4.5 to 8.5. The tonicity of such compositions can be adjusted to either hypotonicity, isotonicity or hypertonicity relative to normal tears by use of generally used materials known to the art. Sodium chloride and mannitol are preferred tonicity agents.

The mechanism of action which explains the utility of retinoids in the compositions of the present invention is not clear at this time. However, it has been found that the retinoids are effective in reversing keratinization and enhancing normal reepithelialization of the cornea.

The compositions of the present invention are useful as ocular lubricants and in the treatment of dry eye syndrome and related ophthalmic surface disorders. The dosage regimen utilized with the liquid preparations of the present invention is typically one or two drops dispensed from a standard ophthalmic dropping device, such as, glass or plastic dropping pipets or plastic bottles fitted with a dropper orifice. Individual drops are within the range of 5 to 75 mg. The drops are placed onto the corneal or sclera surface or into the lower conjunctival sac. The dosage regimen utilized with the solid and semisolid preparations of the present invention is typically 5–75 mg, preferably 25–50 mg, placed into the lower conjunctival sac of the affected eye. Frequency of dosing is variably dependent upon the severity of the condition, but will typically be one to four times per day.

The compositions of the present invention contain an effective amount of retinoid to be dosed only at intervals sufficient to maintain the desired therapeutic effect. The dose and frequency will be critical to prevent a toxic effect. However, there may be a preferred dosage regimen wherein the retinoid provides remission and is no longer required or is only required on a periodic prophylactic basis. It may be necessary in some cases to provide a separate product to dose the eye in between doses of retinoid so as to maintain the corneal epithelium in a hydrated state and provide additional lubrication, thereby reducing irritation and discomfort and enhancing tear film stability. This adjunctive product must be formulated so as to provide these beneficial effects while at the same time minimizing any potential toxicity to the somewhat compromised epithelial cells which could result from the usual preservatives contained in existing artificial tear products. It is therefore preferred to provide an adjunctive product in a sterile form but with no preservative. Another preferred method of providing the desired adjunctive product would be to use a low concentration of a preservative agent which has little or no surface activity, for example, a polyquat such as Onamer-M or similar polyquats. Onamer-M at a concentration of 0.001 wt. % is an effective preservative yet has almost no effect on the corneal epithelial cells. The adjunctive product would contain lubricating and mucomimetic polymers such as methylcellulose, dextran, polyvinylalcohol, polyvinylpyrrolidone, polyethylene glycol, carbomer, polyox, and particularly combinations thereof. These products may be dosed as frequently as required without any concern for adverse effects.

The following Examples are intended to further illustrate, but not to limit, the compositions of the present invention. The term "Retinoid" in these Examples is intended to represent any of the retinoids identified above. All percentages are by weight based on the total weight of the respective compositions.

EXAMPLE 1

The following formulation further illustrates the compositions of the present invention which utilize substantially nonaqueous liquid vehicles.

| Component | Wt. % |
| --- | --- |
| Retinoid | 0.0005 |
| Methylparaben | 0.05 |
| Propylparaben | 0.01 |
| Propyl Gallate | 0.05 |
| Liquid Lanolin (anhydrous) | 3.0 |
| Corn Oil | q.s. 100 |

This composition may be prepared as follows. First, the lanolin and corn oil are combined and heated to a temperature of 40°–45° C. to form a liquid mixture. The remaining components are then dissolved in this liquid mixture. The resulting solution, while under nitrogen pressure, is then passed through a sterilizing membrane filter which is compatible with nonaqueous liquids and has been previously sterilized by means of dry heat. The sterilized solution is then collected in a sterile container.

EXAMPLE 2

The following formulation further illustrates the compositions of the present invention which utilize semisolid vehicles.

| Component | Wt. % |
| --- | --- |
| Retinoid | 0.005 |
| Propyl Gallate | 0.05 |
| Methylparaben | 0.05 |
| Propylparaben | 0.01 |
| Anhydrous Lanolin | 3.0 |
| Corn Oil | 20.0 |
| White Petrolatum | q.s. 100 |

This composition may be prepared by dissolving the propyl gallate in the corn oil at 90° C. and dissolving the methylparaben and propylparaben in the lanolin at 90° C. The two resulting solutions are then combined to form a single solution. The retinoid is then dissolved in this solution at a temperature of 70° C. or higher. The retinoid-containing solution is then combined with the white petrolatum at 90° C. to form the final product. Sterilization of the product may be achieved by filtration through a sterilizing membrane according to known techniques, such as the techniques described in Example 1 above.

EXAMPLE 3

The following formulation further illustrates the compositions of the present invention which utilize a bioerodible solid vehicle.

| Component | Wt. % |
| --- | --- |
| Microfine Retinoid Particles | 0.005 |
| Hydroxyethylcellulose | 49.95 |
| Carbopol 934P | 50.0 |

This composition may be prepared as follows. The retinoid is first sterilized by dissolving it in a suitable solvent, such as diethyl ether, and filtering the resulting solution through a solvent-inert sterilizing membrane. Sterilized retinoid crystals are then recovered from sterilized ethanol. The dried crystals are subjected to an aseptic particle size reduction treatment so that 90% or more of the resulting microfine particles have a maximum dimension (i.e., diameter) of less than 10 microns. These microfine retinoid particles are then aseptically mixed with a sterile, anhydrous powder consisting of an approximately 50:50 mixture of hydroexethylcellulose and Carbopol 934P. The resulting powder mixture is then compressed using a Carver press to form a rod-shaped ocular insert. A small amount of a plasticizer, such as polyethylene glycol or polypropylene glycol, may optionally be added to the above-described powders to improve cohesion of the powders.

EXAMPLE 4

The following formulation further illustrates the compositions of the present invention which utilize an aerosol vehicle.

| Component | Wt. % |
| --- | --- |
| Microfine Retinoid Particles (at least 90% of which have a maximum dimension of 10 microns or less) | 0.0001 |
| Propellant (a mixture of Propellants 11 and 12 in a ratio of 65:35) | 99.9 |

This composition may be prepared by placing the above components into a Medihaler ™ dispenser having a Riker metered valve and an eyecup.

EXAMPLE 5

The following formulation further illustrates the compositions of the present invention which utilize a liquid or semisolid vehicle comprising oil or lipid material and a substantial amount of water in the form of a dispersion mixture.

| Component | Wt. % |
| --- | --- |
| Retinoid | 0.0005 |
| Corn Oil | 20.0 |
| Phospholipid (purified lecithin) | 10.0 |
| Propyl Gallate | 0.05 |
| Methylparaben | 0.05 |
| Propylparaben | 0.01 |
| Hydroxyethylcellulose | 2.0 |
| Purified water | q.s. 100 |

This composition may be prepared by heating the corn oil to 70°–90° C. and then dissolving the retinoid, the parabens and the propyl gallate therein. The resulting solution is cooled to about 40° C., and the powdered lecithin is then dispersed therein to form an oil mixture. A 2% (w/v) solution of hydroxyethylcellulose in water is then slowly added to this mixture under high shear agitation to form a uniform dispersion of the oil mixture in the hydroxyethylcellulose solution. This composition must be shaken well before use.

EXAMPLE 6

The following formulation further illustrates the compositions of the present invention which utilize substantially aqueous vehicles.

| Component | Wt. % |
| --- | --- |
| Retinoid | 0.001 |
| Polyethylene Glycol 300 | 15.0 |
| Polyoxyl 40 Stearate | 5.0 |
| Chlorobutanol | 0.5 |
| Povidone | 3.0 |
| Purified water | q.s. 100 |

This composition may be prepared by dissolving the povidone in water and then dissolving the chlorobutanol in this solution, followed by addition of the polyethylene glycol 300 and polyoxyl 40 stearate. The retinoid is then dissolved in this solution, and the resulting solution is then sterilized by means of appropriate filtration.

The present invention has been described above in connection with certain preferred embodiments. However, as obvious variations thereon will become apparent to those skilled in the art, the invention is not to be considered as limited thereto.

What is claimed is:

1. A method of treating dry eye syndrome which comprises applying topically to the affected eye a therapeutically effective amount of a topical, ophthalmic, pharmaceutical composition comprising 0.00001% to 0.01% by weight of a retinoid of formula:

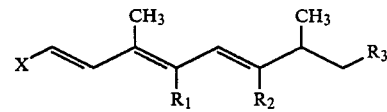

wherein:
  $R_1$ and $R_2$ are selected from hydrogen and fluorine, provided that if one of $R_1$ or $R_2$ is fluorine the other is hydrogen;
  $R_3$ is selected from formyl, hydroxymethyl, alkoxymethyl, carboxyl, and alkoxycarbonyl; and
  X is selected from

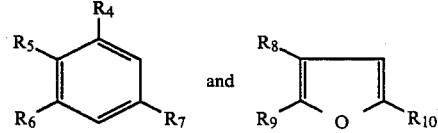

wherein:
  at least one of $R_4$, $R_5$ and $R_7$ is halogen and the other are hydrogen or lower alkyl;
  $R_6$ is selected from lower alkyl and lower alkoxy;
  $R_8$ and $R_{10}$ are each lower alkyl; and
  $R_9$ is selected from hydrogen and lower alkyl, or pharmaceutically acceptable salts thereof; and a pharmaceutically acceptable ophthalmic vehicle.

2. A method according to claim 1, wherein the pharmaceutically acceptable ophthalmic vehicle comprises a non-aqueous semisolid vehicle selected from the group consisting of petrolatum; lanolin and lanolin derivatives; gelled mineral oil having a hydrocarbon base;

petrolatum and ethylene carbonate mixtures; and petrolatum in combination with surfactants and polyglycol.

3. A method according to claim 1, wherein the composition further comprises an effective amount of an antioxidant selected from the group consisting of propyl gallate, hydroquinone, BHA and BHT.

4. A method of treating dry eye syndrome which comprises applying topically to the affected eye a therapeutically effective amount of a topical, ophthalmic, pharmaceutical composition comprising 0.00001% to 0.01% weight of a retinoid of formula:

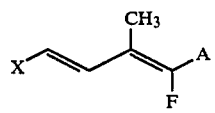

wherein:

A is selected from —CH$_2$OH and —CHO; and

X is selected from

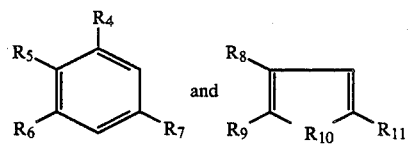

wherein:
at least one of R$_4$, R$_5$ and R$_7$ is halogen and the others are hydrogen or lower alkyl;
R$_6$ is lower alkyl or lower alkoxy;
R$_8$ and R$_{11}$ each are lower alkyl;
R$_9$ is hydrogen or lower alkyl; and
R$_{10}$ is oxygen or sulphur; and a pharmaceutically acceptable ophthalmic vehicle.

5. A method according to claim 4, wherein the pharmaceutically acceptable ophthalmic vehicle comprises a non-aqueous semi-solid vehicle selected from the group consisting of petrolatum; lanolin and lanolin derivatives; gelled mineral oil having a hydrocarbon base; petrolatum and ethylene carbonate mixtures; and petrolatum in combination with surfactants and polyglycol.

6. A method according to claim 4, wherein the composition further comprises an effective amount of an antioxidant selected from the group consisting of propyl gallate, hydroquinone, BHA and BHT.

* * * * *